United States Patent [19]

Dickason et al.

[11] 4,220,595
[45] Sep. 2, 1980

[54] OXIDATION OF BUTANE TO MALEIC ANHYDRIDE

[75] Inventors: Alan F. Dickason, Chester; Wesley R. Cherry, Prospect Park, both of Pa.

[73] Assignee: Sun Ventures, Inc., St. Davids, Pa.

[21] Appl. No.: 407,346

[22] Filed: Oct. 17, 1973

[51] Int. Cl.² .......................................... C07D 307/60
[52] U.S. Cl. ................................ 260/346.75; 252/437
[58] Field of Search ....................... 260/346.8, 346.75; 252/435, 437

[56] References Cited

U.S. PATENT DOCUMENTS

| | | | |
|---|---|---|---|
| 3,005,831 | 10/1961 | Dreibebis | 260/346.8 |
| 3,106,569 | 10/1963 | Robinson | 260/346.8 |
| 3,156,705 | 10/1964 | Kerr | 260/346.8 |
| 3,255,212 | 6/1966 | Kerr | 260/346.8 |
| 3,255,213 | 6/1966 | Kerr | 260/346.8 |
| 3,293,268 | 12/1966 | Bergman et al. | 260/346.8 |
| 3,366,648 | 1/1968 | Kerr | 260/346.8 |
| 3,832,359 | 8/1974 | Freerks et al. | 260/346.8 |
| 3,856,824 | 12/1974 | Raffelson et al. | 260/346.8 |
| 3,862,146 | 1/1975 | Boghosian | 260/346.8 |
| 3,867,411 | 2/1975 | Raffelson et al. | 260/346.8 |

FOREIGN PATENT DOCUMENTS

| | | | |
|---|---|---|---|
| 40-7888 | 4/1965 | Japan | 260/346.8 |
| 145571 | 3/1962 | U.S.S.R. | 260/346.8 |

Primary Examiner—Henry R. Jiles
Assistant Examiner—Bernard Dentz
Attorney, Agent, or Firm—J. Edward Hess; Donald R. Johnson; Stanford M. Back

[57] ABSTRACT

A catalyst comprising A—V—P, where A is an alkaline earth metal, has been found to be effective in the oxidation of butane to maleic anhydride. The catalyst may be employed in combination with an inert support such as $TiO_2$. This catalyst is characterized in having high selectivity and stability over extended periods of time.

3 Claims, No Drawings

OXIDATION OF BUTANE TO MALEIC ANHYDRIDE

BACKGROUND OF THE INVENTION

This invention relates to a novel method for the catalytic vapor phase oxidation of butane with oxygen or air to maleic anhydride wherein there is employed as the catalyst system phosphorus, vanadium and an alkaline earth metal selected from the group consisting of calcium, magnesium, and barium. Desirably, these metals may be incorporated on an inert support such as $TiO_2$.

The vapor phase oxidation of butane to maleic anhydride using various combination of metals, metal salts and/or oxides as catalysts is well known in the art as shown, for example, in German Pat. No. 2,138,692 (Fe/V/Sb/MoO, plus one additional metal); or U.S. Pat. No. 3,293,268 (V/P). U.S. Pat. No. 3,478,063 teaches the oxidation of butene to maleic anhydride using a V/P catalyst containing one other metal, but this patent expressly teaches that butane is inert to this catalyst. See also U.S. Pat. Nos. 3,156,705 and 3,156,706 which also teach the oxidation of butene with like three-component catalyst systems. None of these references, however, discloses the instant catalyst system disclosed herein, nor suggests that it is effective, under the reaction conditions employed, for the oxidation of butane to maleic anhydride with high space-time yields.

SUMMARY OF THE INVENTION

It has now been found, in accordance with the present invention, that a catalyst comprising vanadium, phosphorus, and an alkaline earth metal selected from the group consisting of calcium, magnesium and barium, preferably supported on $TiO_2$, provides an effective catalyst for the oxidation of butane to maleic anhydride. This catalyst system is characterized in particular by its high selectivity and stability over long periods of time.

PREPARATION OF THE CATALYST

As shown by the following examples, the method of preparing the catalyst is not critical, although the phosphorus component should most preferably be derived from the phosphate salt of the akaline earth metal. Thus, for example, a calcium-phosphorus-vanadium catalyst useful in this process may be prepared by adding a solution of vanadyl oxalate to calcium phosphate, followed by addition of phosphoric acid; this mixture is then dried, ground up and calcined at about 450° C. for several hours. Alternatively magnesium or barium phosphate may be employed to form the corresponding catalyst.

In a like manner, when it is desired to include an inert support for the vanadium-phosphorus catalyst, such as $TiO_2$, the same method as described above may be employed, except that the $TiO_2$ is admixed with the calcium phosphate in the initial steps.

It will be understood that in addition to the vanadium, phosphorus, and other metal components illustrated above in the preparation of the catalyst employed in the process of this invention, there may also be employed other salts and/or oxides of the desired components, or even the elements themselves. Thus, for example, the vanadium may be in the form of $V_2O_5$, ammonium vanadate, vanadium acetate, vanadium formate, and like organovanadium compounds, while the phosphorus may be supplied as $P_2O_5$ or as the metal phosphate salts as enumerated above. Alternatively, as stated above, these metals may be combined in compounds with the other catalyst components such as vanadates, or other phosphates, such as acid phosphates, pyrophosphates, or metaphosphates. Of these, as aforestated, calcium phosphate is preferred when a calcium-phosphorus-vanadium catalyst is desired.

The percentage of each of the components in the catalyst composition, should desirably be from about 5 to 50 mole percent of vanadium, as $V_2O_5$, preferably from 8 to 25 percent; from about 5 to 80 mole percent of phosphorus, as $P_2O_5$, preferably 50 to 80 percent; and from about 1 to 50 mole percent of alkaline earth metal as its oxide, preferably 10 to 35 percent. The optimum ratio of each of these catalyst components to each other may easily be determined by routine experimentation, based on the desired balance between selectivity to maleic anhydride and actively based on butane conversion.

In addition to the active ingredients, the catalysts may, if desired contain up to 90 percent, preferably from about 10 to 30 percent, by weight, of the total catalyst, of an inert carrier. Suitable carriers, in addition to $TiO_2$, include aluminum oxide and silicon dioxide.

The active components of the finished catalyst may be present in different forms, generally as the oxides or phosphates, as stated above.

One method of preparing the catalysts employed in the process of this invention is illustrated in the following examples.

CATALYST PREPARATION

EXAMPLE 1

Calcium: Vanadium: Phosphorus

A warm solution of vanadyl oxalate (9.75 gm) in formamide (16.25 gm) and distilled water (12.5 gm) is added to calcium phosphate $(Ca_3(PO_4)_2: \times H_2O$, 23.75 gm), stirring with a plastic spatula until the powder is all wetted. Phosphoric acid (85% $H_3PO_4$, 29.0 gm) is then added and stirred until thoroughly mixed.

The mixture is then evaporated to a thick paste on a steam bath, and dried at 110°–120° C. for 16 hours. The dried cake is broken to pass a 4-mesh screen, calcined from 25°–450° C. over 1 hour, and then held at 450° C. for 6 hours.

EXAMPLE 2

Calcium: Vanadium: Phosphorus-$TiO_2$

A warm solution of vanadyl oxalate (9.75 gm) in formamide (16.25 gm) and distilled water (12.5 gm) is added to a mixture of ferric phosphate $(Ca_3(PO_4)_2: \times H_2O$, 23.75 gm) and titanium dioxide ($TiO_2$, 11.25 gm), stirring with a plastic spatula until the powder is all wetted. Phosphoric acid (85% $H_3PO_4$, 29.0 gm) is then added and stirred until thoroughly mixed.

The mixture is then evaporated to a thick paste on a steam bath, and dried at 110°–120° C. for 16 hours. The dried cake is broken to pass a 4-mesh screen, calcined from 25°–450° C. over 4 hours and then held at 450° C. for 4 hours.

OXIDATION OF BUTANE TO MALEIC ANHYDRIDE

The vapor phase oxidation of butane to maleic anhydride, using the aforedescribed catalysts, may conveniently be carried out by passing the butane, together with oxygen and/or air over a bed of said catalyst at temperatures of from about 500°–650° C., and preferably about 550°–600° C., at contact times of from about 0.001 sec. to 10 sec., and preferably about 0.1 to 2 sec., and at pressures ranging from atmospheric pressure to about 100 lbs./in.$^2$, where the catalyst bed may be either a fixed bed, a fluidized bed, or a moving bed. The concentration of oxygen in the feed stream may vary within moderately wide limits but should desirably be from about 1 to 20 percent by volume of the total feed stream, and preferably about 10 to 20 percent, while the volume of butane contained in the feed should desirably be from about 0.1 to 10 percent and preferably 1 to 5 percent. It will be understood that the oxygen may be diluted with inert gases, or supplied as air.

The maleic anhydride may be recovered from the reaction product by any conventional method, for example, by passing the effluent through water, then stripping off the water. The catalyst may, when necessary, be readily regenerated by treating it with air or oxygen at the reaction temperature.

The use of the aforedescribed catalysts in the oxidation of butane will now be illustrated by the following examples.

EXAMPLE 3

A gaseous mixture of butane (1.0 mole %) and air (99.0 mole %) is passed over 2.0 mls (1.17 g) of a vanadium, calcium, phosphorus catalyst prepared as described in Example 1, contained in a ¼"×6" stainless steel reactor. The contact time is 0.23 sec. at 550° C. The selectivity to maleic anhydride is 39 mole % at 25% conversion.

EXAMPLE 4

A gaseous mixture of butane (1.0 mole %) and air (99.0 mole %) is passed over 2.0 mls (1.30 g) of a vanadium, calcium, phosphorus, catalyst supported on titanium dioxide as described in Example 2, contained in a ¼"×6" stainless steel reactor. The contact time is 0.18 sec. at 550° C. Typical results are summarized in Table I below.

TABLE I

| % C$_4$ V/Ca/P/TiO$_2$ | T, °C. | C$_t$(sec) | GHSV | % Conversion | % Selectivity |
|---|---|---|---|---|---|
| 1 | 550 | .18 | 3600 | 27 | 40 |
| 1 | 550 | .18 | 3600 | 28 | 39 |

The following two comparative examples illustrate the preparation and relative ineffectiveness for oxidation of butane to maleic anhydride of a vanadium-phosphorus catalyst on a TiO$_2$ support, i.e. a catalyst lacking the alkaline earth metal component. This catalyst has the same ratio of vanadium to phosphorus (as phosphoric acid) as described in Example 2.

EXAMPLE 5

Vanadyl oxalate (9.75 g), formamide (16.25 g) and distilled water (12.5 g) were warmed to about 60° C. with constant stirring until completely dissolved. Titanium dioxide (11.25 g) was then added to the warm solution and mixed thoroughly. The mixture was added to 85% phosphoric acid (29.0 g) and evaporated to a thick paste with constant stirring on a steam bath. The paste was dried at 125° C. for 16 hours, crushed and sieved to 10 to 20 mesh, and calcined from 25 to 450° C. over one hour, then held at 450° C. for 6 hours.

EXAMPLE 6

A gaseous mixture of butane (1.0 mole %) and air (99.0 mole %) was passed over 2.0 mls (1.0 g) of a vanadium phosphorus catalyst supported on titanium dioxide (prepared as described in Example 5) contained in a ¼"×6" stainless steel reactor. The contact time was 0.20 sec. at 550° C. No conversion of the butane occurred under these conditions. However, when the reaction mixture was changed to 65% butane and 35% oxygen at 0.20 sec. contact time and 550° C., the conversion was 0.5% to CO$_2$. This example shows that the third component (CA, Mg, or Ba) is absolutely necessary to effect the conversion of butane to maleic anhydride.

INCREASED C$_4$:O$_2$ RATIO

In a further embodiment of the invention it has been found that when the concentration of butane, relative to the amount of oxygen, is increased in the feed stream, the selectivity for maleic anhydride is likewise increased significantly. Customarily, as in the above-described process, the concentration of hydrocarbon in the feed stream is kept low for safety purposes, i.e. at mol ratios of about 1:4 or lower of hydrocarbon to oxygen, and preferably ratios of 1:10 or lower, e.g. 1:20. Under these conditions, it has been found that the selectivity for maleic anhydride is generally between 25 and 50%.

It has now been found that, contrary to general practice and expectations, when the oxygen is employed as pure oxygen rather than diluted with inert gases, e.g. with nitrogen as in air, and the concentration of butane relative to the oxygen is increased to ratios of greater than 1:4, preferably greater than 1:1, in order to operate outside the explosive limits, the selectivity for maleic anhydride is increased about 20% over what is obtained with a hydrocarbon—lean feed but without any dangerous side effects. Thus, it has been found that ratios of greater than 1:4 may be employed, and preferably ratios in the range of about 1:1 to 20:1 of hydrocarbon to oxygen. Furthermore, a significant increase in space-time-yield is obtained when the C$_4$=:O$_2$ ratio is changed and pure oxygen is employed in place of air.

This feature is of great economic significance when designing a commercial plant. There is an obvious advantage with the higher STY in that the reactor size can be substantially reduced.

EXAMPLE 7

A gaseous mixture of butane (65 mole %) and oxygen (35 mole %) is passed over 2.0 mls (1.3 gms) of a vanadium, calcium, phosphorus, catalyst supported on titanium dioxide as described in Example 2, contained in a ¼"×6" stainless steel reactor. The contact time is 0.19 sec. at 500° C. The selectivity to maleic anhydride is 56 mole % at 0.51% conversion.

The invention claimed is:

1. A process for the vapor phase oxidation of butane to form maleic anhydride which comprises reacting butane with air or oxygen at a temperature of about 500°–650° C. in the presence of a catalyst composition consisting essentially of
    (a) vanadium, phosphorous, oxygen and at least one alkaline earth metal selected from the group consisting of calcium, magnesium, and barium, wherein said catalyst contains from about 5–50 mole percent vanadium, 5–80 mole percent phosphorous, and from about 1–50 mole percent of said alkaline earth metal, based on the total metals of the compositon, (b) said catalyst optionally containing a carrier, and the mole ratio of butane to oxygen in the feed stream is no greater than 1:4.

2. A process for the vapor phase oxidation of butane to form maleic anhydride which comprises reacting butane with oxygen or air at temperatures of from about 500° C. to 650° C. in the presence of a catalyst composition consisting essentially of vanadium, phosphorus, and an alkaline earth metal selected from the group consisting of calcium, magnesium and barium, wherein said catalyst contains from about 5 to 50 mole percent vanadium, 5 to 80 mole percent phosphorus, and from about 1 to 50 mole percent of said alkaline earth metal, based on the total metals of the composition, wherein said catalyst composition is supported on $TiO_2$, and wherein the contact time of the butane with the catalyst is from about 0.01 to 10 seconds and the mole ratio of butane to oxygen in the feed stream is no greater than about 1:10.

3. The process according to claim 2 wherein the alkaline earth metal is calcium.

* * * * *